US009676682B2

(12) United States Patent
Goldman et al.

(10) Patent No.: US 9,676,682 B2
(45) Date of Patent: Jun. 13, 2017

(54) CATALYST COMPLEX AND USE THEREOF IN ALKANE OLIGOMERIZATION

(71) Applicants: Alan Stuart Goldman, Highland Park, NJ (US); Robert J. Saxton, San Rafael, CA (US); Oleg Mironov, Hercules, CA (US)

(72) Inventors: Alan Stuart Goldman, Highland Park, NJ (US); Robert Timothy Stibrany, Long Valley, NJ (US); Robert J. Saxton, San Rafael, CA (US); Oleg Mironov, Hercules, CA (US)

(73) Assignees: Chevron U.S.A. Inc., San Ramon, CA (US); Rutgers, The State University of New Jersey, New Brunswick, NJ (US)

( * ) Notice: Subject to any disclaimer, the term of this patent is extended or adjusted under 35 U.S.C. 154(b) by 281 days.

(21) Appl. No.: 14/483,008

(22) Filed: Sep. 10, 2014

(65) Prior Publication Data

US 2015/0073185 A1    Mar. 12, 2015

Related U.S. Application Data

(60) Provisional application No. 61/876,061, filed on Sep. 10, 2013.

(51) Int. Cl.

| | |
|---|---|
| *B01J 21/00* | (2006.01) |
| *B01J 23/00* | (2006.01) |
| *B01J 25/00* | (2006.01) |
| *B01J 29/00* | (2006.01) |
| *B01J 31/00* | (2006.01) |
| *C07C 5/03* | (2006.01) |
| *C07C 5/333* | (2006.01) |
| *C07C 5/48* | (2006.01) |
| *C07C 2/32* | (2006.01) |
| *C07C 5/52* | (2006.01) |
| *B01J 31/02* | (2006.01) |
| *B01J 31/18* | (2006.01) |
| *B01J 31/24* | (2006.01) |

(52) U.S. Cl.
CPC ............. *C07C 5/03* (2013.01); *B01J 31/0208* (2013.01); *B01J 31/183* (2013.01); *B01J 31/2409* (2013.01); *C07C 2/32* (2013.01); *C07C 5/333* (2013.01); *C07C 5/48* (2013.01); *C07C 5/52* (2013.01); *B01J 2231/20* (2013.01); *B01J 2231/766* (2013.01); *B01J 2531/824* (2013.01); *B01J 2531/827* (2013.01); *B01J 2531/828* (2013.01); *C07C 2531/02* (2013.01); *C07C 2531/14* (2013.01); *C07C 2531/22* (2013.01); *C07C 2531/24* (2013.01)

(58) Field of Classification Search
USPC ........................................ 502/172, 100, 150
See application file for complete search history.

(56) References Cited

U.S. PATENT DOCUMENTS

| | | | | |
|---|---|---|---|---|
| 5,017,543 | A | * | 5/1991 | De Clippeleir ........ B01J 23/58 502/328 |
| 5,198,511 | A | * | 3/1993 | Brown-Wensley .... C08G 61/08 526/113 |
| 5,780,701 | A | * | 7/1998 | Kaska ...................... B01J 31/18 556/13 |
| 6,037,297 | A | | 3/2000 | Stibrany et al. |
| 6,689,928 | B2 | | 2/2004 | Stibrany et al. |
| 8,524,963 | B2 | | 9/2013 | Baker et al. |
| 2013/0090503 | A1 | | 4/2013 | Goldman et al. |

FOREIGN PATENT DOCUMENTS

WO      2013052253      4/2013

OTHER PUBLICATIONS

International Search Report from corresponding PCT Application PCT/US2014/055027 mailed Dec. 24, 2014.
Liu, F. et al., "Dehydrogenation of n-Alkanes Catalyzed by Iridium "Pincer" Complexes: Regioselective Formation of α-Olefins", J. Am. Chem. Soc. 121:4086-4087 (1999).
Belli, J. and Craig M. Jensen, "Catalytic Alkane Dehydrogenation by IrClH2 (PPri3)2: Evidence for an Alkane Associative Mechanism", Organometallics 15(6):1532-1534 (1996).
Fan, Hua-Jun and Michael B. Hall, "Density functional studies of catalytic alkane dehydrogenation by an iridium pincer complex with and without a hydrogen acceptor", Journal of Molecular Catalysis A: Chemical 189(1):111-118 (2002).
Burk, M. J. and Robert H. Crabtree, "Selective Catalytic Dehydrogenation of Alkanes to Alkenes", J. Am. Chem. Soc. 109: 8025-8032 (1987).
Crabtree, R.H., et al., "Alkane dehydrogenation by iridium complexes", J. Am. Chem. Soc., 104(1):107-113 (1982).
Burk M. J. et al., "Thermal and Photochemical Catalytic Dehydrogenation of Alkanes with [IrH2(CF3CO2)(PR3)2] (R=C6H4F-p and Cycolhexyl", J. Chem. Soc., Chem. Commun.: pp. 1829-1830 (1985).
Liu, Fuchen and Alan S. Goldman, "Efficient thermochemical alkane dehydrogenation and isomerization catalyzed by an iridium pincer complex", Chem. Comm.: pp. 655-656 (1999).
Jensen, C. M., "Iridium PCP pincer complexes: highly active and robust catalysts for novel homogenous aliphatic dehydrogenations", Chem. Comm.: pp. 2443-2449 (1999).
Gupta, M., et al., "Catalytic dehydrogenation of ethylbenzene and tetrhydrofunan by a dihydrido iridium P—C—P pincer complex", Chem. Commun.: pp. 461-462 (1997).
Singleton, John T., "The uses of pincer complexes in organic synthesis", Tetrahedron 59: pp. 1837-1857 (2003).
Albrecht, M. and Gerard van Koten, "Platinum Group Organometallics Based on "Pincer" Complexes: Sensors, Switches, and Catalysts", Angew. Che. Int. Ed. 40: pp. 3750-3781 (2001).

* cited by examiner

*Primary Examiner* — James McDonough
(74) *Attorney, Agent, or Firm* — E. Joseph Gess; Melissa M. Hayworth

(57) ABSTRACT

Provided is a Group 9 novel metal catalyst complex further comprising a ketone-containing cocatalyst. The metal catalyst complex is useful in generating olefins from alkanes with great efficiency. In one embodiment, provided is an iridium catalyst complex useful in the dehydrogenation of alkanes comprising a ketone-containing cocatalyst and iridium complexed with a tridentate ligand. Also provided is a novel dehydrogenation method which utilizes the catalyst composition. In other embodiments, a novel process for preparing oligomers from alkanes utilizing the catalyst composition is provided.

5 Claims, No Drawings

CATALYST COMPLEX AND USE THEREOF IN ALKANE OLIGOMERIZATION

RELATED APPLICATION

This application claims priority to U.S. Provisional Patent Application No. 61/876,061 filed Sep. 10, 2013, the contents of which are herein incorporated by reference in their entirety.

BACKGROUND OF THE INVENTION

Field of the Invention

Provided is a novel transition metal catalyst complex which can be used in an oligomerization process. More specifically, the novel catalyst complex comprises a Group 9 metal complex and a ketone containing cocatalyst. The catalyst is useful in generating olefins from alkanes, and is useful in oligomerizing alkanes.

Description of the Related Art

Olefins can be generated by direct dehydrogenation with the removal of hydrogen gas or by the use of an acceptor such as ethylene to generate ethane. The chemical industry uses olefins as intermediates in a variety of processes. The largest chemical use is linear α-olefins used in the formation of polyolefins such as ethylene-1-octene copolymers. Also and most importantly, low carbon number olefins have the potential to be converted into higher carbon number molecules that would be suitable for fuels, particularly, diesel. Other products formed from olefins include surfactants, lubricants, and plasticizers.

Iridium complexes as catalysts are known. During the 1980s, it was discovered that certain iridium complexes are capable of catalytically dehydrogenating alkanes to alkenes under exceptionally mild thermal (i.e., less than 160° C.) or even photolytic conditions (see, e.g., *J. Am. Chem. Soc.* 104 (1982) 107; 109 (1987) 8025; *J. Chem. Soc., Chem. Commun.* (1985) 1829). For a more recent example, see *Organometallics* 15 (1996) 1532.

Pincer ligand complexes of rhodium and iridium as catalysts for the dehydrogenation of alkanes are receiving widespread attention. See, for example, F. Liu, E. Pak, B. Singh, C. M. Jensen and A. S. Goldman, "Dehydrogenation of n-Alkanes Catalyzed by Iridium "Pincer" Complexes: Regioselective Formation of α-olefins," *J. Am. Chem. Soc.* 1999, 121, 4086-4087; F. Liu and A. S. Goldman, "Efficient thermochemical alkane dehydrogenation and isomerization catalyzed by an iridium pincer complex," *Chem. Comm.* 1999, 655-656; and C. M. Jensen, "Iridium PCP pincer complexes: highly active and robust catalysts for novel homogenous aliphatic dehydrogenations," *Chem. Comm.* 1999, 2443-2449. The use of compounds such as (PCP)MH$_2$ (PCP=C$_6$H$_3$(CH$_2$PBut$_2$)$_2$-2,6) (M=Rh, Ir) (1a, 1b) dehydrogenate various cycloalkanes to cycloalkenes at 200° C. with turnovers of 70-80 turnovers/hour. The reaction proceeds at 200° C. in neat solvent with or without the use of a sacrificial hydrogen acceptor such as tert-butyl ethylene.

In addition, "pincer" complexes of platinum-group metals have been known since the late 1970s (see, e.g., *J. Chem. Soc.*, Dalton Trans. (1976) 1020). Pincer complexes have a metal center and a pincer skeleton. The pincer skeleton is a tridentate ligand that generally coordinates with the meridional geometry. The use of pincer complexes in organic synthesis, including their use as low-temperature alkane dehydrogenation catalysts, was exploited during the 1990s and is the subject of two review articles (see *Angew. Chem. Int. Ed.* 40 (2001) 3751 and *Tetrahedron* 59 (2003)). See also U.S. Pat. No. 5,780,701. Jensen et al. (*Chem. Commun.* 1997 461) used iridium pincer complexes to dehydrogenate ethylbenzene to styrene at 150 to 200° C. Recently, pincer complexes have been developed that dehydrogenate hydrocarbons at even lower temperatures. For some recent examples, see *J. Mol. Catal.* A 189 (2002) 95, 111 and *Chem. Commun.* (1999) 2443.

In recent years, the chemical industry has employed the use of organometallic catalysts to produce polymers. While many advances in organometallic catalyst technology have been made, researchers continue to seek superior catalyst compositions. In fact, very recently, novel late transition organometallic catalysts have been discovered which are very effectively used in polymerization processes. More specifically, U.S. Pat. No. 6,037,297 to Stibrany et al., herein incorporated by reference, details group IB (Cu, Ag and Au) containing catalyst compositions that are useful in polymerization processes.

Organometallic catalyst technology is also a viable tool in oligomerization processes which produce linear α-olefins for use as feedstock in various other processes. However, one problem often encountered when using many of these catalyst systems is the propensity to produce α-olefins with very low selectivity (i.e., a Schulz-Flory type distribution with high k values). For instance, many of the linear α-olefins made today utilize a neutral nickel (II) catalyst having a planar geometry and containing bidentate monoanionic ligands. While these planar nickel (II) catalysts do produce linear α-olefins, these catalysis systems exhibit a Schulz-Flory type of distribution over a very wide range (i.e., $C_4$-$C_{30+}$).

To address the Schulz-Flory distribution problem, chromium metal based catalysts have become popular for use in certain oligomerization processes. More precisely, chromium complexes have been used to oligomerize ethylene in order to form linear α-olefins with improved distributions. In fact, there has been a report of a specific chromium catalyst which selectively trimerizes ethylene to 1-hexene. These techniques employ the use of a chromium compound in conjunction with aluminoxane along with one of a variety of compounds such as nitrites, amines and ethers. Unfortunately, while these techniques have been able to selectively produce α-olefins, polymer is formed as a co-product. Of course, when polymer is co-produced, the yield of desirable product decreases accordingly. Also, as a practical matter, polymer build-up in the reaction vessel can severely hamper production efficiency thereby limiting the commercial use of such processes.

As discussed above, the organometallic catalyst technology now being used to produce α-olefins has two major disadvantages. First, many of the organometallic catalysts produce α-olefins with a Schulz-Flory type distribution. Unfortunately, this Schulz-Flory type distribution is not ideal when short chain α-olefins are desired—in other words, the selectivity is not good enough to maintain efficient processes. Because α-olefins are used as intermediates for specific products, α-olefins with certain chain lengths are desired. For instance, the following are examples of α-olefin chain lengths that would be desirable as feeds for certain product types: $C_4$ to $C_8$ for comonomer in ethylene polymerization; $C_{10}$ for lube quality poly-α-olefins; and $C_{12}$ to $C_{26}$ for surfactant products. Thus, considerable inefficiency and waste is present when significant amounts of α-olefins are produced having chain lengths outside of the range required for production of a particular chemical. Second, while some of the current organo-metallic catalysts may improve selectivity, most also produce polymer co-product. This lowers the yield of desired product and can also accumulate in the reaction vessel—both of which make commercial use less attractive and inefficient. Hence, there is still a need for improving the selectively and efficiency of linear α-olefin production.

U.S. Pat. No. 6,689,928 describes certain transition metal complexes and the preparation of oligomers using those complexes as catalysts. The starting material is an olefin.

Improvements in catalysts regarding selectivity and efficiency in preparing olefins from alkanes, and being useful in a synthesis of oligomers, particularly alkane oligomers, are still needed. Catalysts which can improve the overall cost and economics of preparing olefins and oligomers from alkanes would be of great benefit to the industry.

SUMMARY OF THE INVENTION

Provided is a Group 9 metal catalyst complex further comprising a ketone-containing cocatalyst. The metal catalyst complex is useful in generating olefins from alkanes with great efficiency. In one embodiment, provided is an iridium catalyst complex useful in the dehydrogenation of alkanes comprising a ketone-containing cocatalyst and iridium complexed with a tridentate ligand. Also provided is a novel dehydrogenation method which utilizes the catalyst composition. In other embodiments, a novel process for preparing oligomers from alkanes utilizing the catalyst composition is provided.

Provided is a process for preparing oligomers from an alkane, comprising (a) contacting an alkane under dehydrogenation conditions in the presence of a dehydrogenation catalyst, e.g., an iridium catalyst complex comprising iridium complexed with a tridentate ligand, to form olefins, and (b) contacting the olefins prepared in step (a) under oligomerization conditions in the presence of an oligomerization catalyst, e.g., a nickel, platinum or palladium metal catalyst complex comprising the metal complexed with a nitrogen containing bi- or tridentate ligand, to prepare oligomers of the olefins, followed by hydrogenation of the coupled olefinic products. In one embodiment, all of the reactions take place in a single reactor, with both the dehydrogenation catalyst and oligomerization catalyst present. The resulting product, after hydrogenation, is an oligomeric alkane.

In one embodiment, the dehydrogenation catalyst of step (a) is an iridium complex of the formula $LMX(X')_n$, where n=0, 1 or 2, X and X' are moieties which can be eliminated from the metal center to generate a catalytically active fragment LM, M is iridium, and L is a tridentate ligand.

In one embodiment, the oligomerization catalyst of step (b) is a metal catalyst complex of the formula $LMX(X')_n$, where n=0, 1 or 2, X and X' are moieties into which a monomer can insert, M is selected from the group consisting of nickel, platinum and palladium, and L is a nitrogen containing bi- or tridentate ligand.

Among other factors, it has been discovered that when a Group 9 metal complex, for example comprising a tridentate ligand, is combined with a ketone-containing cocatalyst, such as benzophenone, a more stable and active catalyst is obtained. The catalyst demonstrates improved activity and lifetime when used in a dehydrogenation reaction as compared to conventional catalysts. Moreover, it has been discovered that by using a dehydrogenation catalyst such as the particular Group 9 metal catalyst complex described above, with a ketone-containing cocatalyst such as benzophenone, and an oligomerization catalyst, such as the particular nickel, palladium or platinum metal catalyst complex described above, an efficient, integrated process for preparing oligomers, and in particular alkane oligomers, is achieved. The process can be practiced in the same reactor with both catalysts present. In the same reactor, the reactions of dehydrogenation and oligomerization will begin to occur simultaneously, as will the hydrogenation reaction of the olefin oligomers to the alkane oligomers. The oligomerization reaction and hydrogenation reaction will actually help drive the overall reaction by using the products of the various reactions. In one embodiment, the ligands for the iridium catalyst complex and the nickel, palladium or platinum metal complex, are the same, i.e., tridentate ligands.

DETAILED DESCRIPTION OF THE INVENTION

Provided is a novel Group 9 metal catalyst complex further comprising a ketone-containing cocatalyst. In one embodiment provided is an iridium catalyst complex useful in the dehydrogenation of alkanes comprising a ketone-containing cocatalyst and iridium complexed with a tridentate ligand. Also provided is a novel dehydrogenation method which utilizes the catalyst composition. In other embodiments, a novel process for preparing oligomers from alkanes utilizing the catalyst composition is provided.

The metal catalyst complex is comprised of a Group 9 metal, e.g., Co. Rh, and Ir, with iridium being preferred. In one embodiment, the metal is associated with tridentate ligands. Examples of suitable metal catalyst complexes include pincer-ligated iridium complexes, both PCP and NCN types. In one embodiment, the metal complex is $(^{ipr}PCP)IrH_4$. In one embodiment the metal, e.g., iridium, is coordinated with a benzimidazolyl-containing ligand to form an NCN type complex.

The cocatalyst comprises a ketone-containing compound. The ketone containing cocatalyst in one embodiment comprises an aryl group. The aryl group can be substituted. The substituted aryl group can independently be chosen from aryls such as but is not limited to, phenyl, naphthyl, anthro, phenanthro, biphenyl, binaphthyl The aryl substitution "R groups" can be independently selected from the group consisting of, but is not limited to, halides, hydride, borates, $C_1$ through $C_{12}$ alky, $C_1$ through $C_{12}$ alkoxy, $C_3$ through $C_{12}$ cycloalkyl, $C_3$ through $C_{12}$ cycloalkoxy, aryl, olefins including diolefins, nitro, and sulfoxides. In one embodiment, benzophenone is the cocatalyst In one embodiment, the present invention, therefore, provides for a catalyst composition of a Group 9 metal complex (e.g., Co, Rh, Ir) with a tridentate ligand and an activating ketone containing cocatalyst as defined above. The preferred ratio of metal complex to activating cocatalyst is from 1:10 to 1:106.

The catalyst composition can be supported. The support material may be a porous material, which includes, but is not limited to, inorganic oxides, zeolites, and inorganic chlorides. The support may also comprise resinous materials such as polystyrene, polyolefin, and other polymeric materials. These catalysts maybe physiosorbed on the support or chemically bonded to the support.

The catalyst composition of the present invention is quite useful in dehydrogenation reactions. The catalyst composition is particularly useful in dehydrogenating alkanes to olefins. Generally, the dehydrogenation may be accomplished utilizing conventional dehydrogenation conditions. Appropriate temperature ranges are from 50 to 250° C. and above, and pressures from about 5 to 30000 psig are acceptable. The most preferred temperature range is from 150 to 250° C. and above, while the preferred pressure is about 15 to 2000 psig.

One issue with "non-oxidative" or "acceptor-less" alkane dehydrogenation is the hydrogen that is co-formed during the process. When chemical reactions are in equilibrium, products must be removed in order for the chemical reaction to proceed further to the right. Also, a build-up of hydrogen can poison a catalyst by preferentially binding to the metal center. Thus, in one embodiment of the present process, alkane dehydrogenation is run with a ($C_{12}$) alkane that boils at high temperature in an open flask. In this way the hydrogen formed is swept out of the reaction medium and the reaction is allowed to proceed.

In "oxidative dehydrogenation", more common in the literature, the dehydrogenation reaction is coupled with oxygen to form water at high temperature. This chemistry is usually run in the gas phase with a heterogeneous catalyst.

In another embodiment, the dehydrogenation process is run in the presence of a hydrogen acceptor, usually a less valuable olefin, where the hydrogen is consumed in a secondary hydrogenation reaction with the acceptor olefin. This is common in a closed system, for example where a low boiling alkane is the reactant. Generally, since an elevated temperature is required for the dehydrogenation reaction, one can use a pressure reactor with a volatile alkane, and in this case an acceptor is required for the reaction to run to any significant conversion.

Furthermore, dehydrogenation may take place in a solvent, neat (e.g., no solvent and liquid condensed olefin), or in gas phase (e.g., olefin in gas phase and catalyst in solid phase). When the dehydrogenation reaction is part of an overall oligomerization reaction, and the oligomerization is conducted in a solvent phase, suitable solvents include, but are not limited to, ethylene, propane, butane, pentane, hexane, toluene, olefins, carbon dioxide, and mixtures thereof.

The alkane starting materials can include straight and branched-chain compounds having from about 1-20 carbon atoms, such as methane, ethane, propane, n-butane, isobutane, n-pentane, n-hexane, 2-methylpentane, 3-methylpentane, heptane, 2-methylheptane, 3-methylheptane, octane, dodecane and the like. In one embodiment, the alkane has from 4-20 carbons. In another embodiment, the alkane is a $C_{12}$ alkane or higher.

The alkane reactant can also be a cycloalkane, where the term "cycloalkane" as used herein should be understood to include macrocyclic cycloalkanes having a carbon ring of 8 or more and up to 25 members and simple cycloalkanes having a carbon ring of less than 8 members but greater than 4 members e.g., cyclopentane, cyclohexane. Typically, the cycloalkane is a $C_5$ to $C_{20}$ membered ring.

These alkane compounds, if desired, may be substituted with various moieties, although care should be taken to exclude substituents which will adversely affect the activity of the catalyst.

The novel composition of the invention can be used in conjunction with an additional cocatalyst that acts to dehydrogenate alkanes in order to provide olefins for oligomerization. Thus, the invention provides a method for providing oligomers from alkanes. A suitable class of dehydrogenation catalysts includes [2,6-bis(di-iso-propylphosphino)phenyl-1 3P,C1,P']iridium dihydride and [2,2'-(1,3-phenylene)bis(1-propylbenzimidazol-2-yl-1κ3N,C,N)iridium hydridobromide]2.

The present invention provides a novel oligomerization method which prepares oligomers from an alkane. The method involves the dehydrogenation of an alkane to prepare olefins, subsequent oligomerization of the olefins, and then hydrogenation to give the alkane. In one embodiment, the catalysts used in each step are specific transition metal catalyst complexes, with the catalyst of the present invention of the catalyst for the dehydrogenation of the alkanes to olefins.

In general, the dehydrogenation reaction, when part of an overall oligomerization reaction, can be run under conventional dehydrogenation reaction conditions, as described above, as long as they are also appropriate for the concurrently run oligomerization. Generally, the reaction can be run at temperatures less than 300° C., even less than 200° C., and in one embodiment, from 150° C. to 250° C. The pressure is adjusted accordingly, and can vary greatly, e.g., from 5 to 30,000 psig. The important aspect is that the conditions are selected to enhance all of the reactions with the catalysts chosen.

The catalyst used for the oligomerization can be any suitable oligomerization catalyst, e.g., a zirconium, hafnium or chromium catalyst. In a specific embodiment, the oligomerization catalyst is also of the formula $LMX(X')_n$, where n=0, 1 or 2, X and X' are independently selected from the group consisting of halides, hydride, triflate, acetates, borates, $C_1$ through $C_{12}$ alky, $C_1$ through $C_{12}$ alkoxy, $C_3$ through $C_{12}$ cycloalkyl, $C_3$ through $C_{12}$ cycloalkoxy, $C_6$ through $C_{14}$ aryl, $C_7$ through $C_{17}$ aralkyl, olefins including diolefins, and any other moiety into which a monomer can insert. M is selected from the group consisting of nickel, palladium, and platinum. L is a nitrogen-containing ligand having two or more nitrogen atoms. In a preferred embodiment L has the formula:

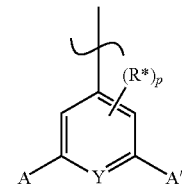

wherein A and A' are independently selected from the group consisting of:

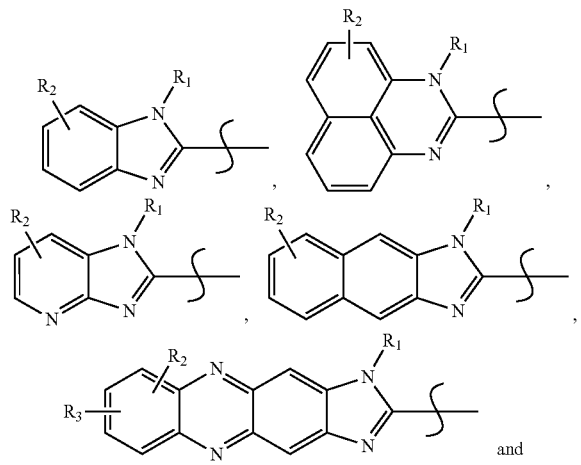

and

-continued

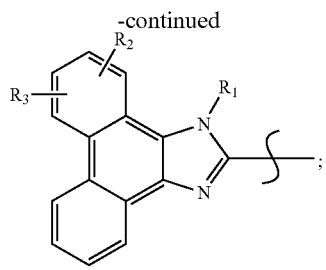

$R_1$, $R_2$, $R_3$ and R* are independently selected from the group consisting of halide, hydride, triflate, acetate, borate, $C_1$ through $C_{12}$ alky, $C_1$ through $C_{12}$ alkoxy, $C_3$ through $C_{12}$ cycloalkyl, $C_3$ through $C_{12}$ cycloalkoxy, $C_6$ through $C_{14}$ aryl, $C_7$ through $C_{17}$ aralkyl and olefins;
and Y is selected from the group consisting of C—H, C—Cl, C—Br, C—I, N, P, C—$OR_4$, wherein $R_4$ is hydrogen, an optionally substituted acyl group, e.g. acetyl or trifluoroacetyl, or a substituted or unsubstituted alkylsulfonyl group, e.g. methylsulfonyl or trifluoromethylsulfonyl and other leaving group; and p=0, 1 or 2.

The nitrogen-containing ligands for the oligomerization catalyst can be synthesized using techniques well known to those skilled in the art. See, for example, U.S. Pat. Nos. 6,037,297 and 6,689,928, foregoing documents being specifically incorporated herein by reference in their entirety. In general, the novel metal catalyst complex can be synthesized by reacting complexing metal salts with the ligands. This can be accomplished, for example, by dissolving the metal salt in a solvent, and then adding the ligand. The mixture is then refluxed and cooled.

The oligomerization catalyst can also be combined with an activating cocatalyst. The activating cocatalyst is selected from the group consisting of alkylalumoxanes, aluminum alkyls, aluminum halides, alkyl aluminum halides, Lewis acids such as tris(pentafluorophenyl)borane, alkylating agents, hydrides such as lithium hydride, reducing agents such as Na/K amalgam, and mixtures thereof. The preferred ratio of metal complex to activating cocatalyst is from $1:10^{-2}$ to $1:10^6$.

The oligomerization catalyst can also be supported. The support material maybe a porous material, which includes, but is not limited to, inorganic oxides, zeolites, and inorganic chlorides. The support may also be resinous materials such as polystyrene, polyolefin, and other polymeric materials. These catalyst maybe physiosorbed on the support or chemically bonded to the support.

Generally, oligomerization may be accomplished utilizing temperatures and pressures used in the prior art. The temperatures and pressures discussed previously are appropriate. The important aspect is that the conditions are selected to best enhance all of the reactions occurring in the reactor with the chosen catalysts.

Once the olefins have been oligomerized, the olefin oligomers are hydrogenated to provide alkane oligomers, i.e., alkanes of higher molecular weight. Hydrogen is present in the reactor from the dehydrogenation, and the catalysts present can also act as catalysts for the hydrogenation reaction. By removing the olefin oligomer products and the hydrogen created by the dehydrogenation reaction, the overall reaction of dehydrogenation to olefins to oligomers is driven to completion.

All the reactions in the reactor can take place in a solvent, neat (e.g., no solvent and liquid condensed olefin), or in gas phase (e.g., olefin in gas phase and catalyst in solid phase). When the reactions are conducted in a solvent phase, suitable solvents include, but are not limited to propane, butane, pentane, hexane, toluene, olefins, carbon dioxide, ionic liquids and mixtures thereof. In one embodiment, toluene is used effectively as the solvent.

In one embodiment, the ligands for the dehydrogenation Group 9 metal catalyst complex and the oligomerization Ni, Pd or Pt metal catalyst complex are the same. The distinct advantages of this are economic and practical. Economically, catalyst synthesis costs would be less if the same ligand is used. From a practical standpoint, using the same ligand eliminates the problems of ligand exchange, thereby leading to a more effective overall process. Using the same ligands even further enhances the efficiency and effectiveness of the present integrated process. In one embodiment, the ligands for the Ir dehydrogenation catalyst and the Ni, Pd or Pt catalyst complexes are benzimidazolyl-containing ligands.

The following examples are provided to further illustrate the present invention, but are not meant to be limiting.

Comparative Example

Acceptorless Dehydrogenation of Dodecane

In an argon-filled glovebox 3.0 mg of [2,6-bis(di-isopropylphosphino)phenyl-1 3P,C1,P']iridium dihydride was placed in a flow-through dehydrogenation apparatus. Then 6.0 mL of n-dodecane was added to give a pale-brown solution with suspended solid. The apparatus was sealed and taken to an Ar Schlenk line. A flow-through rate of about 5 mL/min. was established. The condenser was connected and the reservoir was immersed in a sand bath and a gentle reflux was established. The dehydrogenation was run for 360 hrs. Gas Chromatograph analysis; 0.25% of dehydrogenated products.

Example 1

Acceptorless Dehydrogenation of Dodecane

In an argon-filled glovebox 3.0 mg of [2,6-bis(di-isopropylphosphino)phenyl-1 3P,C1,P']iridium dihydride and 1.0 mg of benzophenone was placed in a flow-through dehydrogenation apparatus. Then 6.0 mL of n-dodecane was added to give a pale-brown solution with suspended solid. The apparatus was sealed and taken to an Ar Schlenk line. A flow-through rate of about 5 mL/min. was established. The condenser was connected and the reservoir was immersed in a sand bath and a gentle reflux was established. The dehydrogenation was run for 360 hrs. GC analysis; 2.36% of dehydrogenated products.

Various modifications and alterations of this invention will become apparent to those skilled in the art without departing from the scope and spirit of the invention. Other objects and advantages will become apparent to those skilled in the art from a review of the preceding description.

A number of patent documents and non-patent documents are cited in the foregoing specification in order to describe the state of the art to which this invention pertains. The entire disclosure of each of the cited documents is incorporated by reference herein.

Furthermore, the transitional terms "comprising", "consisting essentially of" and "consisting of", when used in the appended claims, in original and amended form, serve to indicate what unrecited additional claim elements or steps, if any, are excluded from the scope of the claim(s). The term "comprising" is intended to be inclusive or open-ended and does not exclude any additional, unrecited element, method, step or material. The term "consisting of" excludes any element, step or material other than those specified in the claim and, in the latter instance, impurities ordinary associated with the specified material(s). The term "consisting essentially of" limits the scope of a claim to the specified elements, steps or material(s) and those that do not materially affect the basic and novel characteristic(s) of the claimed invention. All iridium catalyst complexes and methods of use thereof that embody the present invention can, in alternate embodiments, be more specifically defined by any of the transitional terms "comprising", "consisting essentially of" and "consisting of".

That which is claimed is:

1. A catalyst composition useful in the dehydrogenation of alkanes comprising a ketone containing cocatalyst and a Group 9 metal complex, wherein the metal complex is a composition of the formula LMX(X')$_n$, where n=0, 1 or 2;

X and X' are moieties into which a monomer can insert or which can be eliminated from the metal center to generate a fragment LM;

M is a Group 9 metal; and

L is a tridentate ligand with L having the formula:

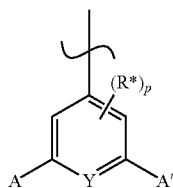

wherein A and A' are independently selected from the group consisting of:

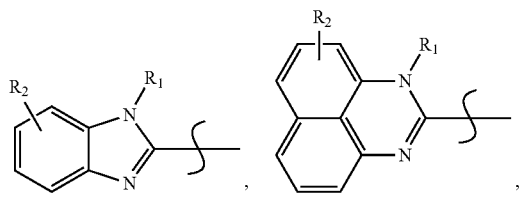

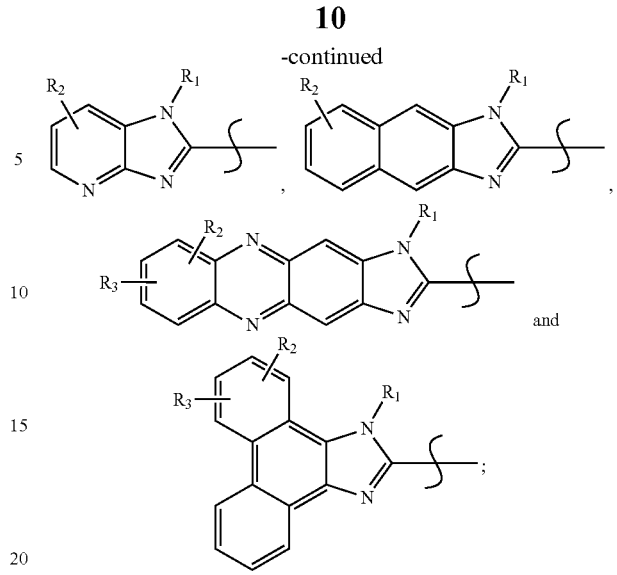

$R_1$, $R_2$, $R_3$ and R* are independently selected from the group consisting of halide, hydride, triflate, acetate, borate, $C_1$ through $C_{12}$ alky, $C_1$ through $C_{12}$ alkoxy, $C_3$ through $C_{12}$ cycloalkyl, $C_3$ through $C_{12}$ cycloalkoxy, $C_6$ through $C_{14}$ aryl, $C_7$ through $C_{17}$ aralkyl and olefins;

and Y is selected from the group consisting of C—H, C—Cl, C—Br, C—I, N, P, C—OR$_4$, wherein R$_4$ is hydrogen, an optionally substituted acyl group, a substituted or unsubstituted alkylsulfonyl group, or other leaving group; and p=0, 1 or 2.

2. The catalyst composition of claim 1, wherein the Group 9 metal is iridium.

3. The catalyst composition of claim 1, wherein the ketone containing cocatalyst comprises benzophenone.

4. The catalyst complex of claim 1, wherein X and X' are independently selected from the group consisting of halides, hydride, triflate, acetates, borates, $C_1$ through $C_{12}$ alky, $C_1$ through $C_{12}$ alkoxy, $C_3$ through $C_{12}$ cycloalkyl, $C_3$ through $C_{12}$ cycloalkoxy, aryl and olefins.

5. The catalyst complex of claim 1, wherein the ligand is 2,6-bis (di-iso-propylphosphino) phenyl-1.

* * * * *